US006593115B2

(12) United States Patent
Vite et al.

(10) Patent No.: US 6,593,115 B2
(45) Date of Patent: Jul. 15, 2003

(54) PREPARATION OF EPOTHILONE INTERMEDIATES

(75) Inventors: Gregory D. Vite, Titusville, NJ (US); Soong-Hoon Kim, Lawrenceville, NJ (US); Gerhard Höfle, Braunschweig (DE)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 09/811,808

(22) Filed: Mar. 19, 2001

(65) Prior Publication Data

US 2002/0042109 A1 Apr. 11, 2002

Related U.S. Application Data

(60) Provisional application No. 60/191,975, filed on Mar. 24, 2000.

(51) Int. Cl.$^7$ .................................................. C12P 7/64
(52) U.S. Cl. ....................... 435/134; 435/135; 435/280; 435/148; 435/136; 435/197; 435/198
(58) Field of Search ................................ 435/148, 134, 435/280, 135, 136, 147, 198

(56) References Cited

U.S. PATENT DOCUMENTS

| 6,194,181 B1 | 2/2001 | Hofmann et al. |
| 6,204,388 B1 | 3/2001 | Danishefsky et al. |

FOREIGN PATENT DOCUMENTS

| DE | 4138042.8 | 5/1993 |
| DE | 19542986.9 | 5/1997 |
| DE | 19639456.2 | 5/1997 |
| DE | 19636343.8 | 3/1998 |
| DE | 19645361.5 | 4/1998 |
| DE | 19645362.3 | 4/1998 |
| DE | 19647580.5 | 5/1998 |
| DE | 19701758 | 7/1998 |
| DE | 19707505.3 | 9/1998 |
| DE | 19713970 | 10/1998 |
| DE | 19720312 | 11/1998 |
| DE | 19821954 | 11/1998 |
| DE | 19726627 | 12/1998 |
| EP | 879 605 | 11/1998 |
| WO | 93/10121 | 5/1993 |
| WO | 97/19086 | 5/1997 |
| WO | 98/08849 | 3/1998 |
| WO | 98/22461 | 5/1998 |
| WO | 98/24427 | 6/1998 |
| WO | 98/25929 | 6/1998 |
| WO | 98/38192 | 9/1998 |
| WO | 98/47891 | 10/1998 |
| WO | 99/01124 | 1/1999 |
| WO | 99/03848 | 1/1999 |
| WO | 99/07692 | 2/1999 |
| WO | 99/39694 | 8/1999 |
| WO | 99/42602 | 8/1999 |
| WO | 99/43320 | 9/1999 |
| WO | 99/43653 | 9/1999 |
| WO | 00/00485 | 1/2000 |
| WO | 00/37473 | 6/2000 |
| WO | 00/66589 | 11/2000 |

OTHER PUBLICATIONS

Bornscheuer et al., Biotechnol. Bioeng. (1998) 58(5), 554–559.*
U.S. patent application Ser. No. 08/856,533, Nicolaou et al., filed May 14, 1997.
U.S. patent application Ser. No. 08/923,869, Nicolaou et al., filed Sep. 4, 1997.
U.S. patent application Ser. No. 60/032,864, Nicolaou et al., filed Dec. 13, 1996.
Balog, A., et al., "Total Synthesis of (–)–Epothilone A", *Angew. Chem. Int. Ed. Engl.*, vol. 35, No. 23/24, 2801–2803 (1996).
Bertini, F., et al., "Alkenes from Epoxides by Reductive Elimination with Magnesium Bromide–Magnesium Amalgam", *Chem. Commun.*, 144 (1970).
Bollag, D.M., et al., "Epothilones, A New Class of Microtubule–stabilizing Agents with a Taxol–like Mechanism of Action", *Cancer Res.* 55, No. 11, 2325–2333 (1995).
Fujisawa, T., et al., "Deoxygenation of Epoxides to Olefins with FeCl$_3$–n–BuLi System", *Chem. Lett.*, 883–886 (1974).
Fujiwara, Y., et al., "Reductive Coupling of Carbonyl Compounds to Olefins by Tungsten Hexachloride–Lithium Aluminum Hydride and Some Tungsten and Molybdenum Carbonyls", *J. Org. Chem.*, vol. 43, No. 12, 2477–2479 (1978).
Gladysz, J. A., et al., "Deoxygenation of Epoxides by Metal Atom Cocondensation", *J. Org. Chem.*, vol. 41, No. 22, 3647–3648 (1976).
Hofle, G., et al., "Epothilone A and B—Novel 16–Membered Macrolides with Cytotoxic Activity: Isolation, Crystal Structure, and Conformation in Solution", *Angew. Chem. Int. Ed. Engl.*, vol. 35, No. 13/14, 1567–1569 (1996).
Hofle, G., et al., "N–Oxidation of Epothilone A–C and O–Acyl Rearrangement to C–19 and C–21 –Substituted Epothilones", *Angew. Chem. Int. Ed.*, vol. 38, No. 13/14, 1971–1974 (1999).
Inokuchi, T., et al., "Opening of Epoxides to Olefins or Halohydrins with Vanadium(II)–Tetrahydrofuran or Vanadium(III)–Tetrahydrofuran Complexes", *Synlett*, No. 6, 510–512 (1992).

(List continued on next page.)

*Primary Examiner*—Irene Marx
(74) *Attorney, Agent, or Firm*—Rena Patel

(57) ABSTRACT

The present invention relates to a process for the preparation of intermediates useful in the synthesis of epothilone analogs by initially enzymatically degrading certain epothilone compounds to form ring-open structures containing a carboxyl group which is esterified, the hydroxyl groups on the moiety protected and the resulting compound oxidized by, e.g. ozone, to form a first intermediate. The first intermediate can be reacted with a triphenylphosphine adduct to yield a compound containing an ester group at position 1 which is subsequently hydrolyzed to form a second intermediate.

4 Claims, No Drawings

OTHER PUBLICATIONS

Kowalski. R. J., et al., "Activities of the Microtubule–stabilizing Agents Epothilones A and B with Purified Tubulin and in Cells Resistant to Paclitaxel (Taxol®)" *J. Biol. Chem.*, vol. 272, No. 4, 2534–2541 (1997).

Kupchan, S. M., et al., "Reductive Elimination of Epoxides to Olefins with Zinc–Copper Couple", *J. Org. Chem.*, vol. 36, No. 9, 1187–1190 (1971).

Martin, M. G., et al., "Epoxides as Alkene Protecting Groups. A Mild and Efficient Deoxygenation", *Tetrahedron Letters*, vol. 25, No. 3, 251–254 (1984).

McMurry, J. E., et al., "Reduction of Epoxides to Olefins with Low Valent Titanium", *J. Org. Chem.*, vol. 40, No. 17, 2555–2556 (1975).

McMurry, J. E., et al., "Some Deoxygenation Reactions with Low–Valent Titanium (TiCl$_3$/LiAlH$_4$)", *J. Org. Chem.*, vol. 43, No. 17, 3249–3254 (1978).

Meng, D., et al., "Remote Effects in Macrolide Formation Through Ring–Forming Olefin Metathesis: An Application to the Synthesis of Fully Active Epothilone Congeners", *J. Am. Chem. Soc.*, vol. 119, No. 11, 2733–2734 (1997).

Nicolaou, K. C., et al., "An Approach to Epothilones Based on Olefin Metathesis", *Angew. Chem. Int. Ed. Engl.*, vol. 35, No. 20, 2399–2401 (1996).

Nicolaou, K. C., et al., "Total Synthesis of Epothilone A: The Macrolactonization Approach", *Angew. Chem. Int. Ed. Engl.*, vol. 36, No. 5, 525–527 (1997).

Nicolaou, K. C., et al., "Designed Epothilones: Combinatorial Synthesis, Tubulin Assembly Properties, and Cytotoxic Action against Taxol–Resistant Tumor Cells", *Angew. Chem. Int. Ed. Engl.*, vol. 36, No. 19, 2097–2103 (1997).

Nicolaou, K.C., et al., "The Olefin Metathesis Approach to Epothilone A and Its Analogues", *J. Am. Chem. Soc.*, vol. 119, No. 34, 7960–7973 (1997).

Nicolaou, K. C., et al., "Total Syntheses of Epothilones A and B via a Macrolactonization–Based Strategy", *J. Am. Chem. Soc.*, vol. 119, No. 34, 7974–7991 (1997).

Nicolaou, K. C., et al., "Synthesis of Epothilones A and B in Solid and Solution Phase", *Nature*, vol. 387, 268–272 (1997).

Nicolaou, K. C., et al., "Synthesis of Epothilones A and B in Solid and Solution Phase" (Correction to *Nature* 387, 268–272 (1997)), *Nature*, 390, 100 (1997).

Raucher, S., et al., "Total Synthesis of (+)–Dihydrocostunolide via Tandem Cope–Claisen Rearrangement", *J. Org. Chem.*, vol. 51, No. 26, 5503–5505 (1986).

Sato, M, et al., "Reduction of Organic Compounds with Low–Valent Niobium (NbCl$_5$/NaAlH$_4$)", *Chem. Letters*, 157–160 (1982).

Schinzer, D., et al., "Total Synthesis of (–)–Epothilone A", *Angew. Chem. Int. Ed. Engl.*, vol. 36, No. 5, 523–524 (1997).

Schobert, R., et al., "Reduction and Isomerization of Oxiranes and α–Diazoketones by Various Early Transition Metallocenes", *Synlett*, vol. 8, 465–466 (1990).

Sharpless, K. B., et al., "Lower Valent Tungsten Halides. A New Class of Reagents for Deoxygenation of Organic Molecules", *J. Amer. Chem. Soc.*, vol. 94, No. 18, 6538–6540 (1972).

Su. D.–S., et al., "Total Synthesis of (–)–Epothilone B: An Extension of the Suzuki Coupling Method and Insights into Structure–Activity Relationships of the Epothilones", *Angew. Chem. Int. Ed. Engl.*, vol. 36, No. 7, 757–759 (1997).

Su D.–S., et al., "Structure–Activity Relationships of the Epothilones and the First In Vivo Comparison with Paclitaxel", *Angew. Chem. Int. Ed. Engl.*, vol. 36, No. 19, 2093–2096 (1997).

Victory, S. F., et al., "Relative Stereochemistry and Solution Conformation of the Novel Paclitaxel–Like Antimitotic Agent Epothilone A", *Bioorg. Med. Chem. Letts.*, vol. 6., No. 7, 893–898 (1996).

Winkler, J. D., et al., "A Model For The Taxol (Paclitaxel)/Epothilone Pharmacophore", *Bioorg. Med. Chem. Letts.*, vol. 6, No. 24, 2963–2966 (1996).

Yang, Z., et al., "Total Synthesis of Epothilone A: The Olefin Metathesis Approach", *Angew. Chem. Int. Ed. Engl.*, vol. 36, No. 1/2, 166–168 (1997).

Bollag, D., et al., "Epothilone, A New Structural Class of Microtubule Stabilizer", Abstract, *Proc. Am. Assoc. Cancer Res.*, vol. 36, 86 Meet. 454 (1995).

Bollag, D., "Epothilones: Novel Microtubule–Stabilising Agents", *Expert Opin. Invest. Drugs*, vol. 6, No. 7, 867–873 (1997).

Bertinato, P., et al., "Studies Toward a Synthesis of Epothilone A: Stereocontrolled Assembly of the Acyl Region and Models for Macrocyclization", J. Org. Chem., vol. 61, No. 23, 8000–8001, (1996).

*Chemical & Engineering News*, "Epothilone Epiphany: Total Syntheses", vol. 74, No. 52, 24–26 (1996).

*Chemical & Engineering News*, "First Total Synthesis of Epothilone B", vol. 75, No. 13, 23 (1997).

*Chemical & Engineering News*, "Solid–Phase Epothilone Synthesis Used to Create Analog Library", vol. 75, No. 20, 33 (1997).

Claus, E., et al., "Synthesis of the C1–C9 Segment of Epothilons", *Tetrahedron Lett.*, vol. 38, No. 8, 1359–1362 (1997).

De Brabander, J., et al., "Towards a Synthesis of Epothilone A: Rapid Assembly of the C1–C6 and C7–C12 Fragments", *Synlett*, vol. 7, 824–826 (1997).

Gabriel, T. and Wessjohann, L., "The Chromium–Reformatsky Reaction: Asymmetric Synthesis of the Aldol Fragment of the Cytotoxic Epothilons from 3–(2–Bromoacyl)–2–Oxazolidinones", *Tetrahedron Lett.*, vol. 38, No. 8, 1363–1366 (1997).

Gerth, K., et al., "Epothilons A and B: Antifungal and Cytotoxic Compounds from *Sorangiusm cellulosum* (Myxobacteria) Production, Physico–chemical and Biological Properties", *J. Antibiotics*, vol. 49, No. 6, 560–563 (1996).

Marshall, A., "Total Synthesis of Epothilone", *Nature Biotechnology*, vol. 15, No. 3, 205 (1997).

Meng, D., et al., "Studies Toward a Synthesis of Epothilone A: Use of Hydropyran Templates for the Management of Acyclic Stereochemical Relationships", *J. Org. Chem.*, vol. 61, No. 23, 7998–7999 (1996).

Meng, D., et al., "Total Syntheses of Epothilones A and B", *J. Am. Chem. Soc.*, vol. 119, No. 42, 10073–10092 (1997).

Mensching, S. and Kalesse, M., "Generation of Thiazoles by Column Dehydrogenation of Thiazolidines with MnO$_2$", *J. Prakt. Chem.*, vol. 339, No. 1, 96–97 (1997).

Mulzer, J. and Mantoulidis, A., "Synthesis of the C(1)–C(9) Segment of the Cytotoxic Macrolides Epothilon A and B", *Tetrahedron Lett.*, vol. 37, No. 51, 9179–9182 (1996).

Nicolaou, K., et al., "Chemistry, Biology and Medicine of Selected Tubulin Polymerizing Agents", *Pure Appl. Chem.*, vol. 71, No. 6 , 989–997 (1999).

Nicolaou, K., et al., "Total Synthesis of Epothilone E and Related Side–chain Modified Analogues Via a Stille Coupling Based Strategy", *Bioorg. Med. Chem.*, vol. 7, No. 5, 665–697 (1999).

Schinzer, D., et al., "Studies Towards the Total Synthesis of Epothilones: Asymmetric Synthesis of the Key Fragments", *Chem. Eur. J.*, vol. 2, No. 22, 1477–1482 (1996).

Taylor, R. and Haley, J., "Towards the Synthesis of Epothilone A: Enantioselective Preparation of the Thiazole Sidechain and Macrocyclic Ring Closure", *Tetrahedron Lett.*, vol. 38, No. 12, 2061–2064 (1997).

Schinzer, D., et al., "Syntheses of (–)–Epothilone A", *Chem. Eur. J.*, vol. 5, No. 9, 2483–2491 (1999).

Schinzer, D., et al., "Syntheses of (–)–Epothilone B", *Chem. Eur. J.*, vol. 5, No. 9, 2492–2500 (1999).

Nicolaou, K. C., et al., "Synthesis and Biological Properties of C12, 13–Cyclopropylepothilone A and Related Epothilones", *Chemistry & Biology*, vol. 5, No. 7, 365–372 (1998).

Altmann, K.H., et al., "Epothilones and Related Structures—A New Class of Microtubule Inhibitors With Patent In Vivo Antitumor Activity," Biochim. Biophys Acta, 1470 (2000).

* cited by examiner

PREPARATION OF EPOTHILONE INTERMEDIATES

CROSS-REFERENCE TO RELATED APPLICATION

This application claims priority from provisional U.S. application Ser. No. 60/191,975, filed Mar. 24, 2000, incorporated herein by reference in its entirety.

FIELD OF THE INVENTION

The present invention relates to an improved process for the preparation of certain epothilone analogs.

BACKGROUND OF THE INVENTION

Epothilones are macrolide compounds that find utility in the pharmaceutical field. For example, epothilones A and B having the structures:

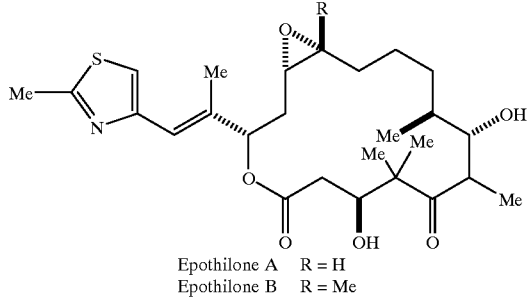

Epothilone A  R = H
Epothilone B  R = Me may be found to exert microtubule-stabilizing effects similar to paclitaxel (TAXOL®) and hence cytotoxic activity against rapidly proliferating cells, such as, tumor cells or other hyperproliferative cellular disease, see Hofle, G., et al., *Angew. Chem. Int. Ed. Engl.*, Vol. 35, No.13/14, 1567–1569 (1996); WO93/10121 published May 27, 1993; and WO97/19086 published May 29, 1997.

Derivatives and analogs of epothilones A and B have been synthesized and may be used to treat a variety of cancers and other abnormal proliferative diseases. Such analogs are disclosed in Hofle et al., Id.; Nicolaou, K. C., et al., *Angew. Chem. Int. Ed. Engl.* Vol. 36, No. 19, 2097–2103 (1997); and Su, D. -S., et al., *Angew. Chem. Int. Ed. Engl.* Vol. 36, No. 19, 2093–2097 (1997).

SUMMARY OF THE INVENTION

The present invention is directed to a process for the preparation of compounds represented by formulas I and II wherein X, $P_1$, $P_2$, $R_1$ and $R_2$ are as defined below:

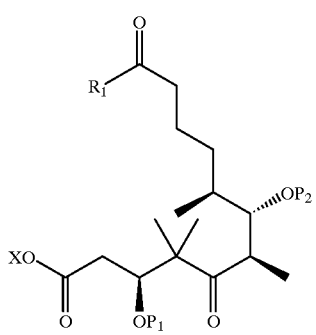

I

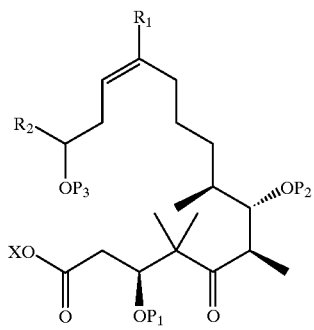

II

The compounds represented by formulas I and II are intermediates for the preparation of epothilone analogs that are useful in the treatment of a variety of cancers and other abnormal proliferative diseases.

DETAILED DESCRIPTION OF THE INVENTION

The process of the present invention provides an advantageous synthesis for the compounds represented by formulas I and II

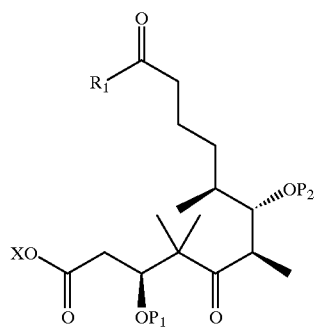

I

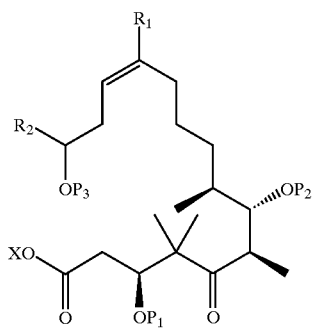

II

Compounds of formula I can be utilized to prepare, for example, analogs represented by formula II which can, in turn, be utilized to prepare epothilone analogs represented by the formulas III and IV.

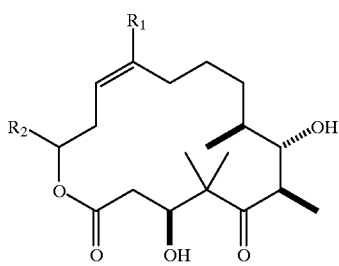

III

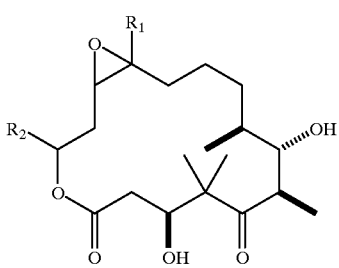

IV

As used in the formulas I, II, III, IV and throughout the specification, the symbols as given below have the following meanings:

X is selected from the group consisting of hydrogen, alkyl, substituted alkyl, aryl and substituted aryl;

$R_1$ is selected from the group consisting of hydrogen, alkyl, substituted alkyl, aryl, substituted aryl, and heterocyclo;

$R_2$ is hydrogen, alkyl, substituted alkyl, aryl, substituted aryl, heterocyclo or

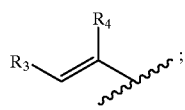;

$R_3$ and $R_4$ are selected from the group consisting of hydrogen, alkyl, substituted alkyl, aryl, substituted aryl, cycloalkyl and heterocyclo;

$P_1$, $P_2$, $P_3$ are independently selected from the group consisting of hydrogen, aralkyl, substituted aralkyl, trialkylsilyl, triarylsilyl, dialkylarylsilyl, diarylalkylsilylalkoxyalkyl, and aralkyloxyalkyl.

Definitions

The following are definitions of various terms used herein to describe this invention. These definitions apply to the terms as they are used throughout this specification, unless otherwise limited in specific instances, either individually or as part of a larger group.

The term "alkyl" refers to optionally substituted straight- or branched-chain saturated hydrocarbon groups having from 1 to 20 carbon atoms, preferably from 1 to 7 carbon atoms. The expression "lower alkyl" refers to optionally substituted alkyl groups having from 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkyoxy, heterocyclooxy, oxo, alkanoyl, aryl, aryloxy, aralkyl, alkanoyloxy, amino, alkylamino, arylamino, aralkylamino, cycloalkylamino, heterocycloamino, disubstituted amino in which the two substituents on the amino group are selected from alkyl, aryl, aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or instances where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Wherein, as noted above, the substituents themselves are further substituted, such further substituents are selected from the group consisting of halogen, alkyl, alkoxy, aryl and aralkyl. The definitions given herein for alkyl and substituted alkyl apply as well to the alkyl portion of alkoxy groups.

The term "halogen" or "halo" refers to fluorine, chlorine, bromine and iodine.

The term "aryl" refers to monocyclic or bicyclic aromatic hydrocarbon groups having from 6 to 12 carbon atoms in the ring portion, for example, phenyl, naphthyl, biphenyl and diphenyl groups, each of which may be substituted.

The term "aralkyl" refers to an aryl group bonded to a larger entity through an alkyl group, such as benzyl.

The term "substituted aryl" refers to an aryl group substituted by, for example, one to four substituents such as alkyl; substituted alkyl, halo, trifluoromethyl, trifluoromethoxy, hydroxy, alkoxy, cycloalkyloxy, heterocyclooxy, alkanoyl, alkanoyloxy, amino, alkylamino, dialkylamino, aralkylamino, cycloalkylamino, heterocycloamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by one or more members selected from the group consisting of halo, hydroxy, alkyl, alkoxy, aryl, substituted alkyl, substituted aryl and aralkyl.

The term "cycloalkyl" refers to optionally substituted saturated cyclic hydrocarbon ring systems, preferably containing 1 to 3 rings and 3 to 7 carbons per ring, which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more of the groups described above as substituents for alkyl groups.

The terms "heterocycle", "heterocyclic" and "heterocyclo" refer to an optionally substituted, unsaturated, partially saturated, or fully saturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents for the terms "heterocycle," "heterocyclic," and "heterocyclo" include one or more substituent groups as described above for substituted alkyl or substituted aryl, and smaller heterocyclos, such as, epoxides, aziridines and the like.

The term "alkanoyl" refers to —C(O)-alkyl.

The term "substituted alkanoyl" refers to —C(O)-substituted alkyl.

The term "heteroatoms" shall include oxygen, sulfur and nitrogen.

The compounds represented by formulas I, II, III, IV above may exist as multiple optical, geometric, and stereoisomers. While the compounds shown herein are depicted for one optical orientation, included within the present invention are all isomers and mixtures thereof.

Use and Utility

The compounds represented by formulas III and IV above are microtubule-stabilizing agents. The compounds, and thus the process, are useful in the treatment of a variety of cancers and other proliferative diseases including, but not limited to, the following:

carcinoma, including that of the bladder, breast, colon, kidney, liver, lung, ovary, pancreas, stomach, cervix, thyroid and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyoscarcoma;

other tumors, including melanoma, seminoma, teratocarcinoma, neuroblastoma and glioma;

tumors of the central and peripheral nervous system, including astrocytoma, neuroblastoma, glioma, and schwannomas;

tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma.

The compounds represented by formulas III and IV above will also inhibit angiogenesis, thereby affecting the growth of tumors and providing treatment of tumors and tumor-related disorders. Such anti-angiogenesis properties of the compounds represented by formulas III and IV will also be useful in the treatment of other conditions responsive to anti-angiogenesis agents including, but not limited to, certain forms of blindness related to retinal vascularization, arthritis, especially inflammatory arthritis, multiple sclerosis, restinosis and psoriasis.

Compounds represented by formulas III and IV will induce or inhibit apoptosis, a physiological cell death process critical for normal development and homeostasis. Alterations of apoptotic pathways contribute to the pathogenesis of a variety of human diseases. Compounds represented by formulas III and IV, as modulators of apoptosis, will be useful in the treatment of a variety of human diseases with aberrations in apoptosis including, but not limited to cancer, particularly but not limited to, follicular lymphomas, carcinomas with p53 mutations, hormone dependent tumors of the breast, prostrate and ovary, and precancerous lesions such as familial adenomatous polyposis, viral infections including but not limited to herpesvirus, poxvirus, Epstein-Barr virus, Sindbis virus and adenovirus, autoimmune diseases such as systemic lupus erythematosus, immune mediated glomerulonephritis, rheumatoid arthritis, psoriasis, inflammatory bowel diseases and autoimmune diabetes mellitus; neurodegenerative disorders such as Alzheimer's disease, AIDS-related dementia, Parkinson's disease, amyotrophic lateral sclerosis, retinitis pigmentosa, spinal muscular atrophy and cerebellar degeneration; AIDS; myelodysplastic syndromes; aplastic anemia; ischemic injury associated myocardial infarctions; stroke and reperfusion injury; restenosis; arrhythmia; atherosclerosis; toxin-induced or alcohol induced liver diseases; hematological diseases such as chronic anemia and aplastic anemia; degenerative diseases of the musculoskeletal system such as osteoporosis and arthritis; aspirin-sensitive rhinosinusitis; cystic fibrosis; multiple sclerosis; kidney diseases; and cancer pain.

The compounds represented by formulas III and IV are also useful in combination with known anti-cancer and cytotoxic agents and treatments, including radiation. If formulated as a fixed dose, such combination products employ the compounds represented by formulas III and IV within the dosage range described below and the other pharmaceutically active agent within its approved dosage range. Compounds represented by formulas III and IV can be used sequentially with known anticancer or cytotoxic agents and treatment, including radiation when a combination formulation is inappropriate. Especially useful are cytotoxic drug combinations wherein the second drug chosen acts in a different phase of the cell cycle, e.g. S phase, than the present compounds represented by formulas III and IV which exert their effects at the $G_2$-M phase.

The compounds prepared in accordance with the present invention can be formulated with a pharmaceutical vehicle or diluent for oral, intravenous or subcutaneous administration. Such pharmaceutical compositions can be formulated in a classical manner well known to those of ordinary skill in the art using solid or liquid vehicles, diluents and additives appropriate to the desired mode of administration.

Orally, the compounds can be administered in the form of tablets, capsules, granules, powders and the like. The compounds are administered in a dosage range of about 0.05 to 200 mg/kg/day, preferably less than 100 mg/kg/day, in a single dose or in 2 to 4 divided doses.

Methods of Preparation

The intermediate compounds represented by formulas I and II are prepared from epothilone compounds represented by formula V in Scheme 1, particularly epothilone C or D wherein $R_1$ is as defined above. The epothilone starting materials will fall under the general formulas III and IV as shown above. The advantage of the subject process is that it can be utilized to transform epothilone compounds that may have less than optimum properties into other analogs that have more desirable properties. The epothilone starting materials represented by formula V and formula XV are known compounds. See, for example, Kim et al., *Org. Lett.*, 2, 1537 (2000); Hofle et al., *Angew. Chem. Int. Ed. Engl.*, 35, 1567–1569 (1996); WO 93/10121 published May 27, 1993; and WO 97/19086 published May 29, 1997; Nicolaou et al., *Angew Chem. Int. Ed. Engl.*, 36, 2097–2103 (1997); and Su et al., *Angew. Chem. Int. Ed. Engl.*, 36, 2093–2097 (1997).

As illustrated in Scheme 1, the epothilone starting material V is treated with a suitable enzyme that causes the molecule to degrade to yield a compound represented by formula VI as illustrated in Scheme 1. Suitable enzymes include, without intended limitation, pig liver esterase, chymotrypsin, or pancreatin. The carboxyl moiety of the compound represented by formula VI is then esterified to form an ester represented by formula VII by treatment with an alkylating agent such as diazomethane, trimethylsilyl diazomethane, or an alkyl halide. In the reaction illustrated in Scheme 1, trimethylsilyldiazomethane is utilized as the alkylating agent to form the methyl ester of the carboxyl moiety.

The ester compounds represented by formula VII are then treated to form protecting groups, such as silanes, on the hydroxyl groups. This is carried out by reaction with suitable agents such as trialkylsilyl halides, triflates, i.e. trifluoromethane sulfonates, to form a compound represented by formula VIII wherein $P_1$, $P_2$ and/or $P_3$ are as defined above. A preferred reagent for forming the protecting groups on the hydroxyls is t-butyldimethylsilyl trifluoromethanesulfonate. The compounds represented by formula VIII are then oxidized, e.g. by ozone, to cleave the olefin at position 12, thereby forming the subject intermediate compounds represented by formula I.

The intermediate compounds of the present invention represented by formula I are suitably converted to the subject intermediate compounds represented by formula II in two steps as shown in Scheme 1. In the first step, the compound represented by formula I is reacted with a suitable Wittig type reagent represented by the following formula

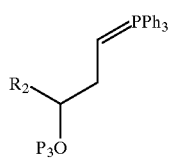

IX wherein $R_2$ and $P_3$ are as defined above, illustrated by formula IX in Scheme 1. The reagents represented by formula IX can be prepared, for example, as described by Nicolaou et al., *Angew. Chem.*, Vol. 110, No. 85 (1998). The reaction of the compound represented by formula IX and the compound represented by formula I in Scheme 1 is an ester represented by formula X in Scheme 1. The ester moiety at position 1 of the compounds represented by formula X is then hydrolyzed by methods well know in the art, e.g. treatment with a suitable base, such as aqueous hydroxides or carbonates, to yield the carboxylic acids represented by formula II.

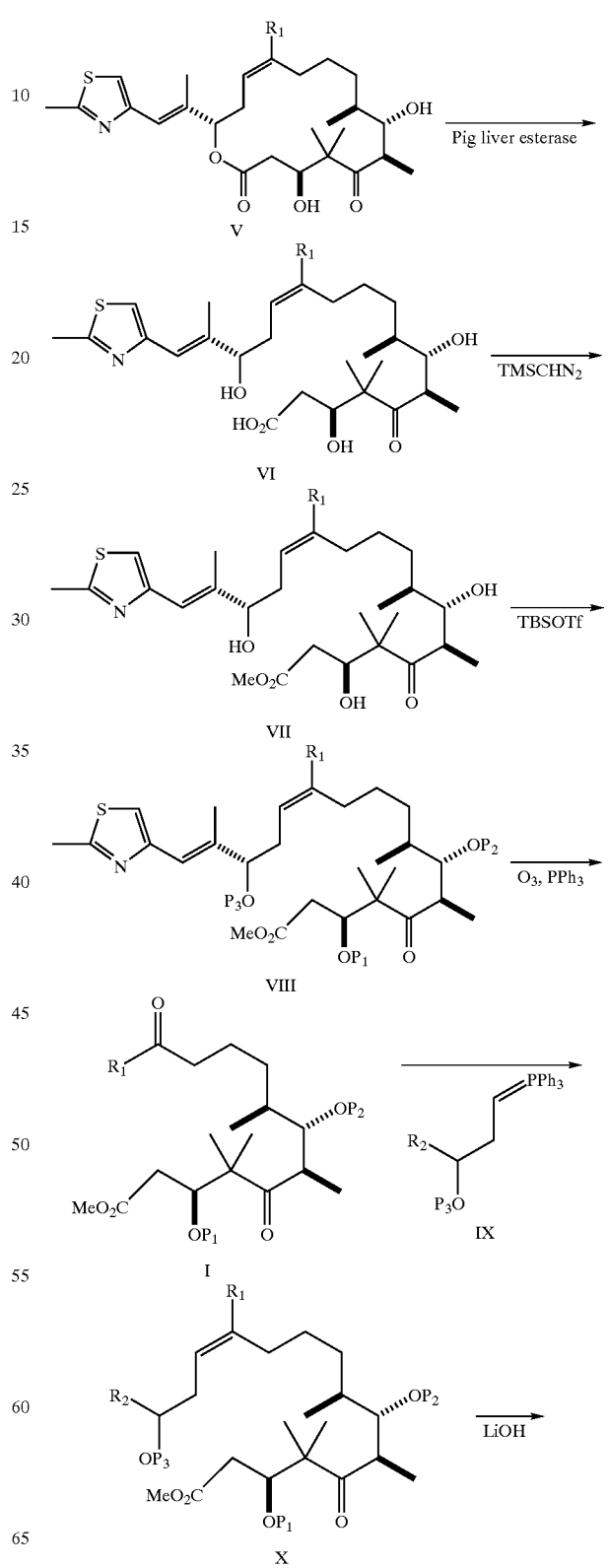

Scheme 1

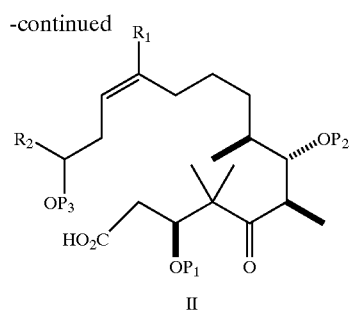

Compounds of formula II and methods for synthesizing epothilone analogs from such compounds are known. See, Nicolaou et al., *J. Amer. Chem. Soc.*, 119, 7974 (1997). The protected hydroxyl groups of compounds of formula II may be deprotected according to several known procedures. See, Greene and Wuts, "Protective Groups In Organic Synthesis," 2nd Ed., John Wiley & Sons, Inc., New York, 1991.

Intermediate compound represented by formula I can also be prepared according to the procedures depicted in Scheme 2.

As illustrated in Scheme 2, the epothilone starting material XV is treated with a suitable enzyme that cleaves the compound of formula XV to form a compound of formula XVI bearing a carboxyl group. Suitable enzymes include, but are not limited to, pig liver esterase, chymotrypsin or pancreatin. The carboxyl group of compound XVI is then esterified with an alkylating agent to form the ester compound XVII. Examples of alkylating agents include, but are not limited to, diazomethane, trimethylsilyl diazomethane or an alkyl halide. As an example, in the reaction depicted in Scheme 2, diazomethane is used as the alkylating agent. The ester compound XVII is next hydrolyzed to form a diol compound of formula XVIII. This hydrolysis step is performed under acidic conditions. Finally, compound XVIII is oxidized to form the intermediate of formula I. An example of an oxidizing agent is sodium periodate. Other examples include, but are not limited to, $Ca(OCl)_2$, $NaBiO_3$, $I(OAc)_3$, $HIO_4$, Amberlite and 904-$NaIO_4$ (*J. Chem. Soc. Perkin I*, 509 (1982)), $Pb(OAc)_2$, HgO and $I_2$, $MnO_2$, $KmnO_4$, $H_2CrO_4$, PCC (*Syn. Commun.*, 12, 833 (1982)), $RuCl_2(PPh_3)_3$ and $BaMnO_4$.

The compounds represented by formulas I and II are useful as intermediates in the preparation of epothilone analogs characterized by enhanced activity.

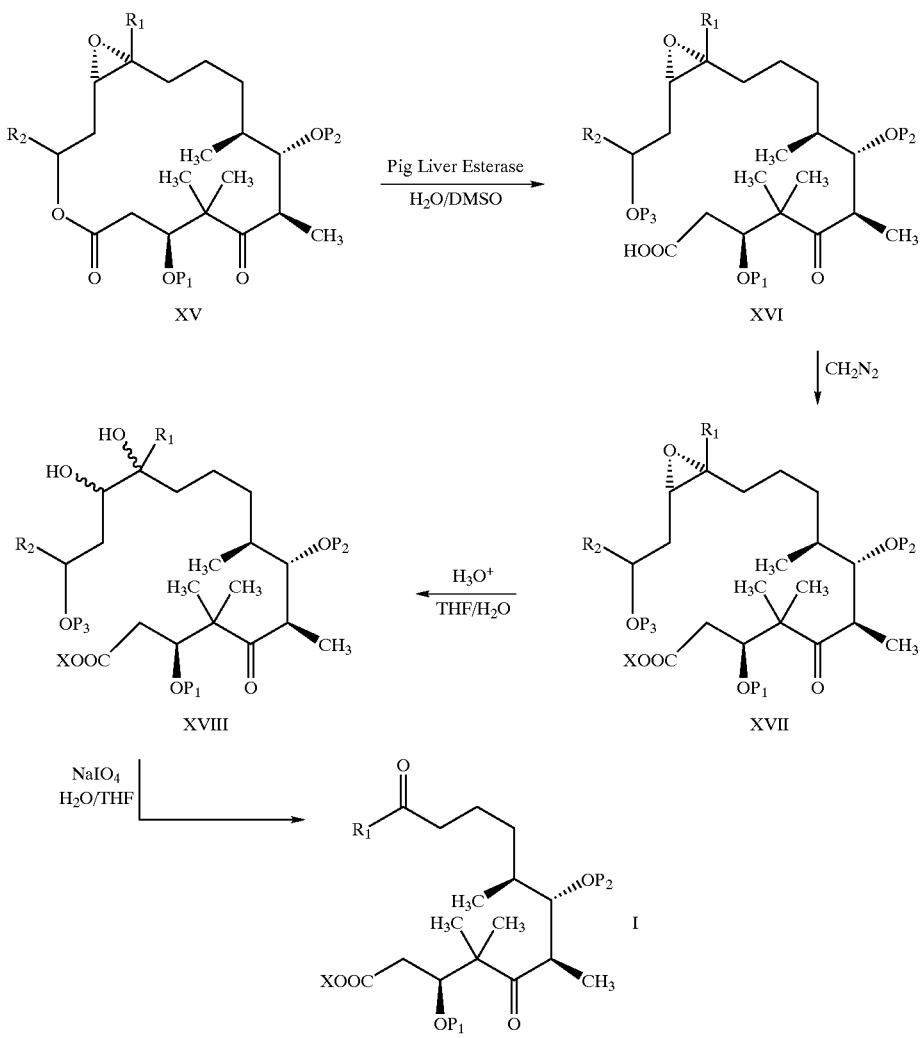

Scheme 2

All references cited herein are incorporated by reference as if set forth at length herein.

The following non-limiting examples serve to illustrate the practice of the invention.

EXAMPLE 1

Preparation of a Compound Represented by the Formula

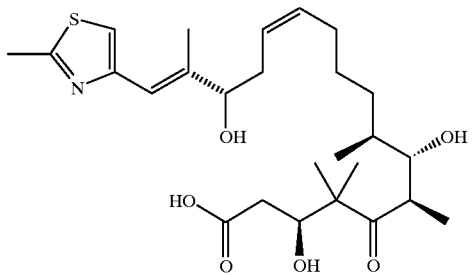

A solution of epothilone C, representative of formula V in Scheme 1 (8.4 mg, 0.017 mmol) in 125 μL dimethylsulfoxide was diluted with 5.0 mL of pH 7 phosphate buffer. Pig liver esterase (200 units in 50 μL of 3.2M aqueous $(NH_4)_2SO_4$) was added, and the suspension was stirred at 37° C. for 18 hours. TLC showed that epothilone C was completely consumed. The reaction was stored at −34° C. for 12 days. The mixture was acidified to pH about 4.5 with 1 N HCl and then extracted with two 5 mL portions of dichloromethane. The organic phase was dried over $Na_2SO_4$, concentrated under vacuum, and purified by flash chromatography on silica gel eluting with 1% acetic acid in ethyl acetate to provide 2.1 mg (25%) of the compound of the formula given above, representative of formula VI in Scheme 1, as a clear film. MS ($ESI^+$): 496 $(M+H)^+$; MS ($ESI^-$): 494 $(M-H)^-$

EXAMPLE 2

Preparation of a Compound Represented by the Formula

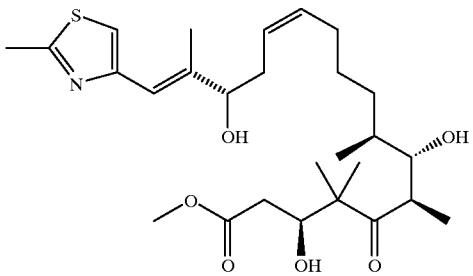

A solution of the compound formed in Example 1 (1 mg, 0.0020 mmol) in 0.5 mL of a mixture of 2:7 methanol:toluene was treated with two drops of trimethylsilyl diazomethane at 25° C. After 10 minutes, TLC showed that the starting material had been converted to a new UV active component. The reaction was concentrated under vacuum and purified by flash chromatography on silica gel eluting with a gradient of 60–100% ethyl acetate in hexane to provide 1 mg (100%) of the compound given above formula given above, representative of formula VII in Scheme 1, as a clear film. MS ($ESI^+$): 510 $(M+H)^+$; MS ($ESI^-$): 508 $(M-H)^-$

EXAMPLE 3

Preparation of a Compound Represented by the Formula

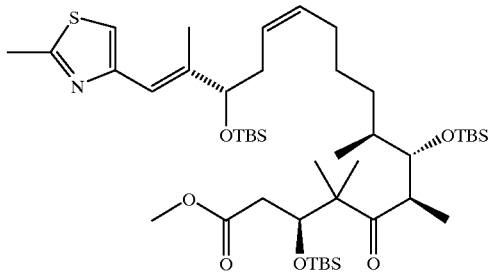

To a solution of the compound formed in Example 2 (20.4 mg, 0.04 mmol) in 2.0 mL anhydrous dichloromethane at −14° C. was added 2,6-lutidine (23 μL, 0.2 mmol, 5 eq). t-Butyldimethylsilyl triflate (32 μL, 0.14 mmol, 3.5 eq) was added dropwise to the reaction. After 30 minutes, additional 2,6-lutidine (33 μL, 0.28 mmol, 7 eq) and t-butyldimethylsilyl triflate (65 μL, 0.28 mmol, 75 eq) were added. After 12 hours, TLC indicated that the starting material had been consumed. Saturated aqueous $NaHCO_3$ (5 mL) was added and the reaction was extracted with two 5 mL portions of dichloromethane. The organic phase was dried over $Na_2SO_4$, concentrated under vacuum, and purified by flash chromatography on silica gel eluting with 10% ethyl acetate in petroleum ether to provide 15 mg (44%) of the compound given above, representative of compound VIII in Scheme 1, as a clear film. MS ($ESI^+$): 838 (M+H-$CH_3$)$^+$

EXAMPLE 4

Preparation of a Compound Represented by the Formula

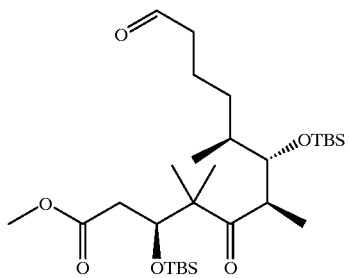

A solution of the compound formed in Example 3 (6.4 mg, 0.0075 mmol) in 2.0 mL anhydrous dichloromethane was cooled to −78° C. Ozone was passed through the solution for approximately 2 minutes, during which time the solution became light blue. Triphenylphosphine (8 mg, 0.03 mmol, 4 eq) was added and the reaction mixture was warmed to room temperature over 30 minutes. The reaction mixture was concentrated under vacuum and purified by flash chromatography on silica gel eluting with 10% ethyl acetate in petroleum ether to provide 3.6 mg (86%) of the compound given above, representative of compound I of the present invention, as a clear film. MS ($ESI^+$): 559 $(M+H)^+$ Preparation of a Compound Represented by the Formula

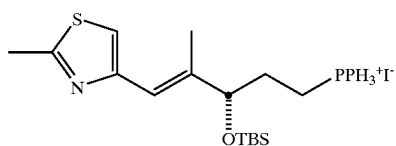

As a separate step, the compound given above, representative of compound IX in Scheme 1, was prepared as described by Nicolaou et al., *Angew. Chem.*, 1998, 110, 85. MS (ESI⁺): 572 (M+H)⁺

EXAMPLE 5

Preparation of a Compound Represented by the Formula

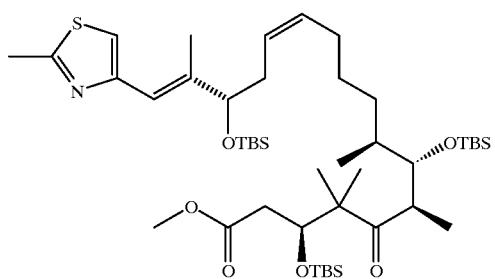

A solution of the compound formed in Example 4 according to the method taught by Nicolaou et al. (18 mg, 0.013 mmol, 2 eq) in 0.5 mL anhydrous tetrahydrofuran was cooled to 0° C. Sodium bis(trimethylsilyl)amide (31 μL, 31 μmol, 2.4 eq) was added and the solution became brown. The reaction was cooled to −20° C. and the compound formed in Example 4 representative of formula I of the present invention (7.3 mg, 0.013 mmol, 1 eq) in 0.5 mL tetrahydrofuran was added. After 10 minutes, the reaction was quenched with 4 mL of saturated aqueous NaHCO₃ and extracted with two 2 mL portions of dichloromethane. The organic phase was dried over Na₂SO₄, concentrated under vacuum, and purified by flash chromatography on silica gel eluting with 10% ethyl acetate in petroleum ether to provide 6 mg (55%) of the compound given above, representative of compound X in Scheme 1, as a clear oil. MS (ESI⁺): 852 (M+H)⁺; 874 (M+Na)⁺

EXAMPLE 6

Preparation of a Compound Represented by the Formula

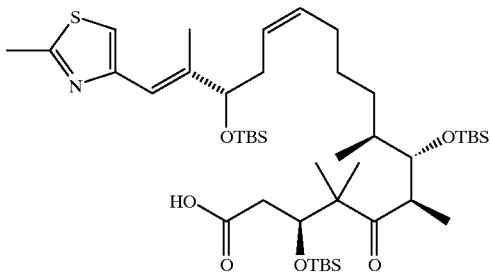

A solution of the ester compound prepared in Example 5 (2.2 mg, 0.0026 mmol) in 0.5 mL t-butyl alcohol/water (2:1) was treated with aqueous 1.0M LiOH (40 μL, 0.039 mmol, 15 eq). The reaction was stirred for 48 hours at room temperature. TLC indicated that the reaction was approximately 50% complete. The reaction was purified by flash chromatography on silica gel eluting with 10% ethyl acetate in hexane with 1% acetic acid to provide 1 mg (46%) of the compound given above, representative of compound II of the present invention.

EXAMPLE 7

Preparation of the Compound Represented by the Formula XIV (Scheme 3)

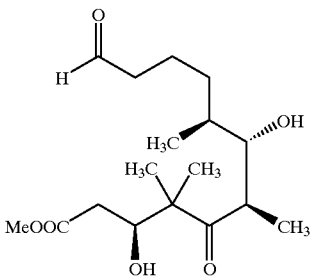

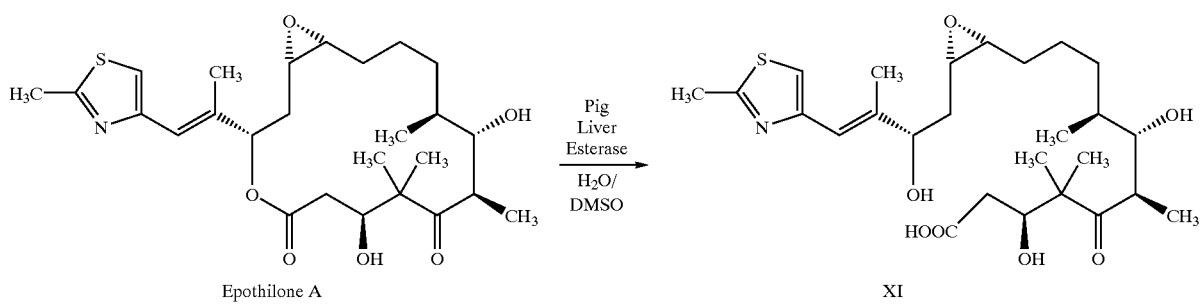

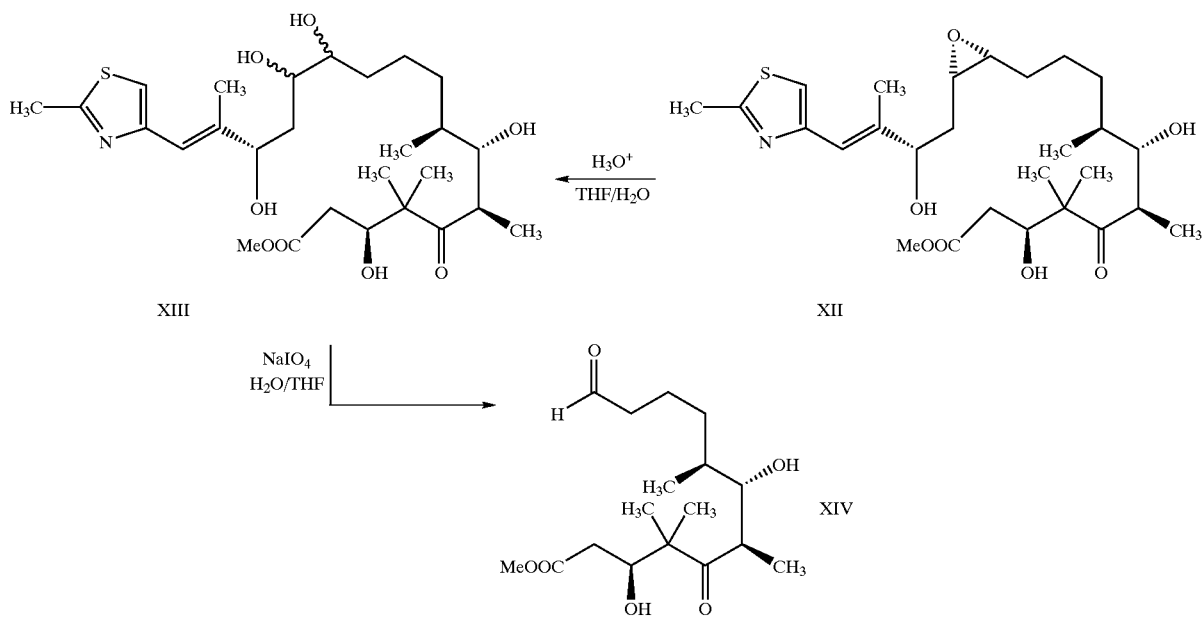

(i) Preparation of compound of formula XI:

Epothilone A (0.5 g, 1.01 mmol) was dissolved in 0.2 mL of DMSO and 300 mL of phosphate buffer (20 mmol, pH 7.4). Pig liver esterase (50 mg) was added to the epothilone A solution, with stirring. After stirring for 3 days, residual lactone was extracted with 50 mL of a 1:1 mixture of hexanes and ethyl acetate. The aqueous phase was adjusted to pH 5 and extracted three times with ethyl acetate. The organic layer was dried with $MgSO_4$, filtered and evaporated. Yield: 0.55 g of compound XI was obtained as a viscous oil containing 10% of solvents.

(ii) Preparation of compound of formula XII:

Compound XI (60 mg) obtained above was dissolved in ethyl acetate. To this, excess diazomethane in diethyl ether was added. The conversion was complete in 15 minutes. The solvents were evaporated in vacuo to yield 50 mg of ester compound XII as a colorless viscous oil.

(iii) Preparation of compound of formula XIII:

Compound XII (23 mg) was dissolved in THF (0.5 mL). To this solution, was added concentrated sulfuric acid (50 mg) dissolved in 1 mL of $H_2O$, with stirring. After one hour, the pH was adjusted to 7 with sodium bicarbonate, and the mixture extracted three times with ethyl acetate. The organic extract was evaporated to provide 21 mg of crude diol compound XIII as a mixture of stereoisomers.

$^1$H-NMR ($CD_3OD$): 7.20, 7.21 (s, 19-H), 6.68, 6.63 (s, 17-H), 4.33 (dd, 3-H), 4.40, 3.76, 3.53, 3.47, 3.36 (m, 7-H, 12-H, 13-H), 3.72 (s, OMe), 2.72 (s, 21-$H_3$), 2.48, 2.37 (ddd, 2-$H_2$), 2.00, 2.02 (s, 16-Me), 1.8–1.3 (m, 8-H, 9-$H_2$, 10-$H_2$, 11-$H_2$), 1.21, 1.18 (s, 4-$(CH_3)_2$), 1.12 (d, 6-Me), 0.96 (d, 8-Me).

(iv) Preparation of compound of formula XIV:

Diol XIII (23 mg) was dissolved in 0.6 mL of THF. To this solution was added sodium periodate (7 mg) in 1.2 mL of $H_2O$, with stirring. After 30 minutes, the solvents were evaporated in vacuo and the residue purified by preparative HPLC (Nucleosil RP 18, methanol/water gradient 35:65 to 60:40). The fraction containing compound XIV was concentrated in vacuo and extracted with n-butanol. Evaporation of the organic layer provided 12 mg of the aldehyde compound XIV.

$^1$H-NMR ($CDCl_3$): 9.76 (t, 12-H), 4.25 (dd, 3-H), 3.73 (s, $OCH_3$), 3.38 (dd, 7-H), 3.25 (dq, 6-H), 2.3 2.5 (m, 2-$H_2$, 11-$H_2$), 1.75 (m, 8-H), 1.55 (m, 9-$H_2$, 10-$H_2$, 11-$H_2$), 1.19, 1.13 (4-$(CH_3)_2$), 1.06 (d, 6-$CH_3$), 0.87 (d, 8-$CH_3$).

ESI-MS (pos. ions): $^m/_z$=357 (M+H$^+$+MeOH).

What is claimed is:

1. A process for preparing a compound of formula I:

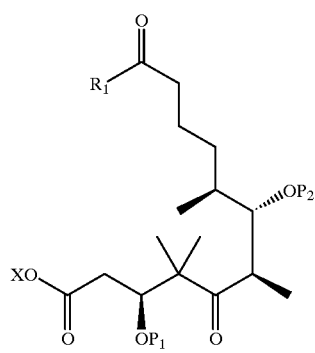

wherein:

X is selected from the group consisting of hydrogen, alkyl, substituted alkyl, aryl and substituted aryl;

$R_1$ is selected from the group consisting of hydrogen, alkyl, substituted alkyl, aryl, substituted aryl, and heterocyclo; and $P_1$ and $P_2$ are independently selected from the group consisting of hydrogen, aralkyl, substituted aralkyl, trialkylsilyl, triarylsilyl, dialkylarylsilyl, diarylalkylsilylalkoxyalkyl, and aralkyloxyalkyl;

comprising treating an epothilone compound of formula III or formula IV:

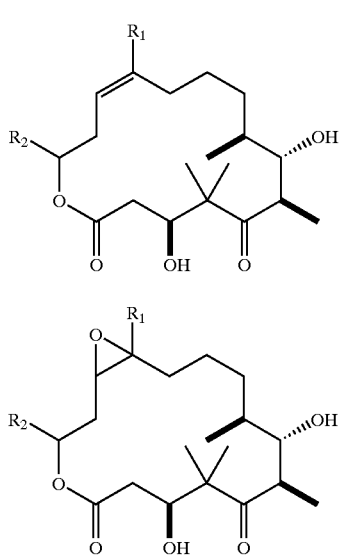

wherein:
R$_1$ is as defined above;
R$_2$ is hydrogen, alkyl, substituted alkyl, aryl, substituted aryl, heterocyclo or

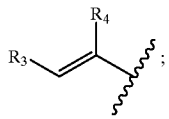

and
R$_3$ and R$_4$ are selected from the group consisting of hydrogen, alkyl, substituted alkyl, aryl, substituted aryl, cycloalkyl and heterocyclo;
with an enzyme selected from the group consisting of chymotrypsin, pancreatin, and an esterase capable of cleaving or degrading said compound to form a compound of formula VI:

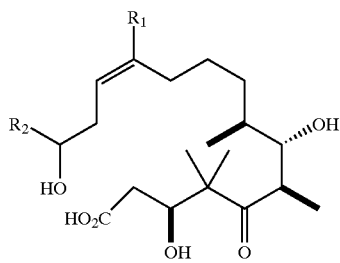

wherein R$_1$ and R$_2$ are as defined above;
optionally esterifying the carboxyl group of said compound;
optionally reacting the resulting esterified compound to form protecting groups on the hydroxyl groups of said compound; and
reacting the resulting compound with a suitable oxidizing agent to form said compound of formula I.

2. A process for preparing a compound of formula II:

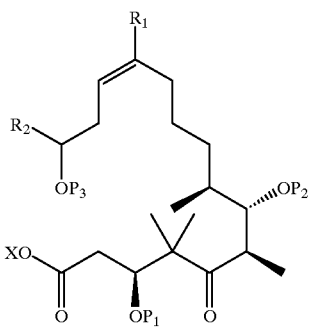

wherein:

X is selected from the group consisting of hydrogen, alkyl, substituted alkyl, aryl and substituted aryl;

R$_1$ is selected from the group consisting of hydrogen, alkyl, substituted alkyl, aryl, substituted aryl, and heterocyclo;

R$_2$ is hydrogen, alkyl, substituted alkyl, aryl, substituted aryl, heterocyclo or

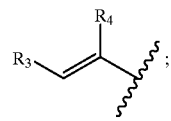

R$_3$ and R$_4$ are selected from the group consisting of hydrogen, alkyl, substituted alkyl, aryl, substituted aryl, cycloalkyl and heterocyclo; and P$_1$, P$_2$, and P$_3$ are independently selected from the group consisting of hydrogen, aralkyl, substituted aralkyl, trialkylsilyl, triarylsilyl, dialkylarylsilyl, diarylalkylsilylalkoxyalkyl, and aralkyloxyalkyl;

comprising treating an epothilone compound of formula III or formula IV:

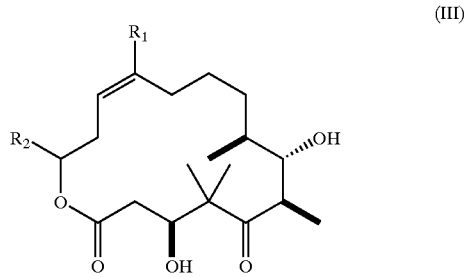

-continued

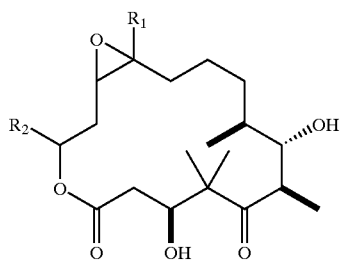
(IV)

with an enzyme selected from the group consisting of chymotrypsin, pancreatin and an esterase capable of cleaving or degrading said compound to form a compound of formula VI:

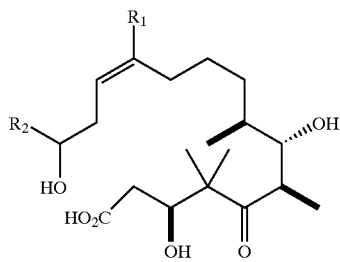
(VI)

esterifying the carboxyl group of said compound;

reacting the resulting esterified compound to form protecting groups on the hydroxyl groups of said compound;

reacting the resulting compound with a suitable oxidizing agent to form a compound of formula I:

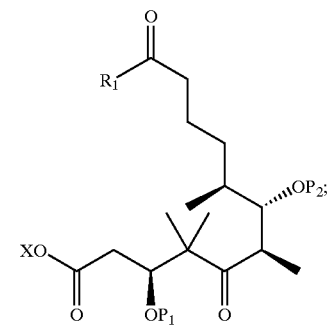
(I)

reacting said compound with a compound of formula IX:

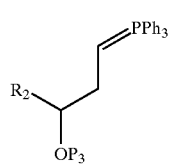
(IX)

to form a compound of formula X:

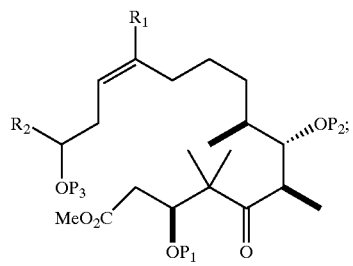
(X)

and hydrolyzing the ester group on said compound in the presence of a suitable base to form said compound of formula II.

3. A process for preparing a compound of formula I:

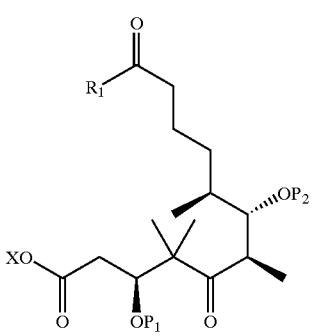
(I)

wherein:

X is selected from the group consisting of hydrogen, alkyl, substituted alkyl, aryl and substituted aryl;

$R_1$ is selected from the group consisting of hydrogen, alkyl, substituted alkyl, aryl, substituted aryl, and heterocyclo; and each $P_1$ and $P_2$ is, independently, selected from the group consisting of hydrogen, aralkyl, substituted aralkyl, trialkylsilyl, triarylsilyl, dialkylarylsilyl, diarylalkylsilylalkoxyalkyl, and aralkyloxyalkyl;

comprising treating an epothilone compound of formula XV:

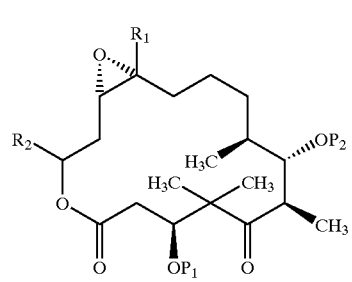
(XV)

wherein:
R₁, P₁ and P₂ are as defined above;
R₂ is hydrogen, alkyl, substituted alkyl, aryl, substituted aryl, heterocyclo or

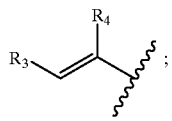

and
R₃ and R₄ are selected from the group consisting of hydrogen, alkyl, substituted alkyl, aryl, substituted aryl, cycloalkyl and heterocyclo;
with an enzyme selected from the group consisting of chymotrypsin, pancreatin and an esterase capable of cleaving or degrading said compound to form a compound of formula XVI:

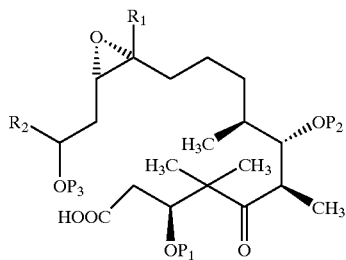

(XVI)

wherein:
R₁, R₂, P₁ and P₂ are as defined above; and
P₃ is selected from the group consisting of hydrogen, aralkyl, substituted aralkyl, trialkylsilyl, triaryisilyl, dialkylarylsilyl, diarylalkylsilylalkoxyalkyl, and aralkyloxyalkyl;

esterifying the carboxyl group of compound of formula XVI to form an ester compound of formula XVII:

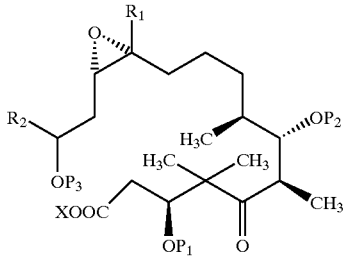

(XVII)

wherein X, R₁, R₂, P₁, P₂ and P₃ are as defined above;
hydrolyzing the ester compound to form a diol compound of formula XVIII:

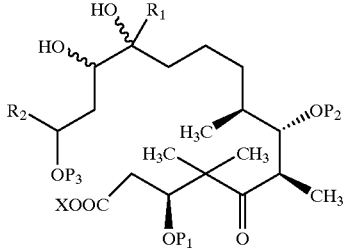

(XVIII)

wherein X, R₁, R₂, P₁, P₂ and P₃ are as defined above; and
reacting the diol compound with a suitable oxidizing agent to form said compound of formula I.

4. The method of claim 1, 2 or 3, wherein the esterase is pig liver esterase.

* * * * *